United States Patent
Zander et al.

(10) Patent No.: US 8,197,455 B2
(45) Date of Patent: Jun. 12, 2012

(54) ABSORBENT ARTICLES AND/OR PACKAGING COMPONENTS EACH HAVING DIFFERENT PATTERNS IN A SINGLE CONTAINER

(75) Inventors: Teresa Marie Zander, Bonduel, WI (US); James Joseph Clark, Jr., Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1288 days.

(21) Appl. No.: 11/020,844

(22) Filed: Dec. 21, 2004

(65) Prior Publication Data
US 2006/0135927 A1      Jun. 22, 2006

(51) Int. Cl.
*A61F 13/15* (2006.01)
*A61L 15/00* (2006.01)
*B65D 73/00* (2006.01)

(52) U.S. Cl. .............. 604/385.01; 604/385.02; 206/438; 206/440; 206/494

(58) Field of Classification Search ............. 604/385.02, 604/385.01; 206/438, 440, 494
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,100,324 A | 7/1978 | Anderson et al. |
| 4,340,563 A | 7/1982 | Appel et al. |
| 4,488,928 A | 12/1984 | Ali Khan et al. |
| 4,589,876 A | 5/1986 | Van Tilburg |
| 4,687,478 A | 8/1987 | Van Tillburg |
| 5,267,992 A | 12/1993 | Van Tilburg |

(Continued)

FOREIGN PATENT DOCUMENTS
EP      1 529 629 A1      5/2005
(Continued)

*Primary Examiner* — Jacqueline F. Stephens
(74) *Attorney, Agent, or Firm* — David J. Arteman; Randall W. Fieldhack (57) ABSTRACT

In the present invention, a packaging component having an outer surface and an interior volume contains within the interior volume a plurality of absorbent personal care articles. Each absorbent personal care article has a garment facing surface and a body facing surface. A portion of the plurality of the absorbent personal care articles in the packaging component are first absorbent articles having a first pattern embossed or printed on at least a portion of one of the surfaces. In addition, a portion of the plurality of the absorbent personal care articles in the packaging component are second absorbent articles having a second pattern is embossed or printed on at least a portion of one of the surfaces. In this aspect of the present invention, the first and second patterns are different from each other in at least one aspect. Further, a portion of the plurality of absorbent personal care articles may also contain additional absorbent articles which have yet another pattern embossed on one of the surfaces. In another aspect of the present invention there are more that two different embossing or printing patterns on the absorbent articles within the package. Generally, in the present invention every absorbent article within a given package may have a different pattern embossed or printed on the body facing surface or the garment facing surface of each of the absorbent articles. Also provided are wrapper components for absorbent articles having different patterns thereon.

29 Claims, 6 Drawing Sheets

U.S. PATENT DOCUMENTS

| | | | |
|---|---|---|---|
| 5,284,703 A | 2/1994 | Everhart et al. | |
| 5,350,624 A | 9/1994 | Georger et al. | |
| 5,489,283 A | 2/1996 | Van Tillburg | |
| 5,503,076 A | 4/1996 | Yeo | |
| 5,897,541 A | 4/1999 | Uitenbroek et al. | |
| 5,967,665 A | 10/1999 | MacDonald et al. | |
| 5,993,430 A | 11/1999 | Gossens et al. | |
| 6,036,679 A | 3/2000 | Balzar et al. | |
| 6,045,900 A | 4/2000 | Haffner et al. | |
| 6,093,027 A * | 7/2000 | Unger et al. | 434/429 |
| 6,276,032 B1 | 8/2001 | Nortman et al. | |
| 6,315,765 B1 | 11/2001 | Datta et al. | |
| 6,387,084 B1 | 5/2002 | Vangompel et al. | |
| 6,491,165 B2 | 12/2002 | Kuske et al. | |
| 6,500,160 B2 | 12/2002 | Mizutani et al. | |
| 6,601,706 B2 | 8/2003 | Mcmanus et al. | |
| 6,658,817 B1 | 12/2003 | Eve et al. | |
| 6,705,465 B2 | 3/2004 | Ling et al. | |
| 6,716,203 B2 | 4/2004 | Sorebo et al. | |
| 6,763,944 B2 * | 7/2004 | Ronn et al. | 206/440 |
| 2001/0008683 A1 | 7/2001 | Takai et al. | |
| 2002/0148749 A1 | 10/2002 | Briseboi et al. | |
| 2003/0073966 A1 | 4/2003 | Sosalla et al. | |
| 2003/0130632 A1 | 7/2003 | Costea et al. | |
| 2003/0229325 A1 | 12/2003 | Belau et al. | |
| 2003/0233081 A1 | 12/2003 | Belau et al. | |
| 2004/0040204 A1 | 3/2004 | Weder | |
| 2004/0040205 A1 | 3/2004 | Weder | |
| 2004/0143231 A1 | 7/2004 | Nair et al. | |
| 2004/0204698 A1 | 10/2004 | Zenker et al. | |
| 2006/0025739 A1 | 2/2006 | Dipalma et al. | |

FOREIGN PATENT DOCUMENTS

| | | |
|---|---|---|
| GB | 2 380 447 A | 4/2003 |
| JP | 05-317357 A | 12/1993 |
| WO | WO 94/23107 A2 | 10/1994 |
| WO | WO 00/13632 A1 | 3/2000 |
| WO | WO 02/096331 | 12/2002 |
| WO | WO 2004/064872 | 8/2004 |
| WO | WO 2006/068673 A1 | 6/2006 |

* cited by examiner

ABSORBENT ARTICLES AND/OR PACKAGING COMPONENTS EACH HAVING DIFFERENT PATTERNS IN A SINGLE CONTAINER

FIELD OF THE INVENTION

The present invention relates generally to personal care products, and in particular, to a personal care article and wrapper or pouch component for a personal care article.

BACKGROUND OF THE INVENTION

Absorbent products intended to absorb discharged body fluids are well known in the art. Such absorbent products generally comprise a fibrous mass or other absorbent body which can absorb and hold body fluids. Similarly, it is well known that feminine care articles have been employed to absorb and hold liquids, such as urine and/or menses. The absorbent articles have included various systems of liquid-handling layers, such as intake layers, distribution layers, retention layers and the like. Additionally, the absorbent articles have included patterns of embossments distributed on the bodyside surface of the article to provide a hinging action, or to inhibit or direct a desired flow of liquids. In a given package of absorbent articles, every absorbent personal care article in the package has essentially the same embossing pattern.

Typically, the absorbent articles are placed in purses, backpacks, briefcases, and the like such that they are loose, and are free to move with in the purses, backpacks, briefcases, and the like with the other items contained therein. Unfortunately, purses, backpacks, briefcases, and the like do not always provide a hygienic environment for the articles, and thus the articles can become dirty and/or damaged. Further, the articles can become scattered about in purses, backpacks, briefcases, and the like so they are difficult to find when needed.

To avoid the problems described above, often personal care products, including for example, feminine pads, tampons and pantiliners and the like, are individually wrapped or are wrapped in groups of 2-5 absorbent articles in a pouch or similar wrapper, which generally includes a flap that closes the pouch or wrapper. The pouches/wrappers and the absorbent personal care articles contained within the pouch/wrapper are generally packaged into an outer packaging component which contains a plurality of the pouches/wrappers and the absorbent article. Typically, such pouches/wrappers are a solid color, or have a pattern that covers the entirety of the pouch/wrapper and each pouch/wrapper within the packaging component is identical to each other. Likewise, the personal care articles contained within the individual pouches/wrappers in the packaging component all have the same design or pattern within any given outer packaging component.

Selecting a particular design for the personal care articles as well as the pouches/wrappers can be a tricky proposition. If a particular design is chosen, it could have a polarizing effect. While being liked by some consumers, other consumers may dislike the design. Those consumers who dislike the design may be more likely to complain about the product, or stop purchasing the product based on their dislike of the design.

In the case of feminine care products, such as sanitary napkins, incontinence pads, pantiliners and the like, there is a need for an absorbent article which can provide a possible emotional benefit to the user. Many females experience a down turn in their mood during the menstrual period. Generally, sanitary napkins have a white color or a simple combination of colors to provide a sanitary appearance. Within a given package of sanitary napkins, each sanitary napkin will look essentially identical to the other sanitary napkins in the package. As a result, the user of the sanitary napkins is provided with essentially no emotional benefit by the appearance of the sanitary napkin. Therefore, there is a need in the art to provide a possible emotional benefit to the users of the feminine care products.

SUMMARY OF THE INVENTION

Generally stated, the present invention provides a way to provide consumers with a variety of designs within a package of absorbent personal care articles.

In the present invention, a packaging component having an outer surface and an interior volume contains within the interior volume a plurality of absorbent personal care articles. Each absorbent personal care article has a garment facing surface and a body facing surface. A portion of the plurality of the absorbent personal care articles in the packaging component are first absorbent articles having a first pattern embossed or printed on at least a portion of one of the surfaces. In addition, a portion of the plurality of the absorbent personal care articles in the packaging component are second absorbent articles having a second pattern that is embossed or printed on at least a portion of one of the surfaces. In this aspect of the present invention, the first and second patterns are different from each other in at least one aspect. Further, a portion of the plurality of absorbent personal care articles may also contain additional absorbent articles which have yet another pattern embossed or printed on one of the surfaces. In another aspect of the present invention there are more that two different embossing or printing patterns on the absorbent articles within the package. Generally, in the present invention every absorbent article within a given package may have a different pattern embossed or printed on the body facing surface or the garment facing surface of each of the absorbent articles.

In a second aspect, the present invention provides a packaging component having an outer surface and an interior volume which has disposed within the interior volume a plurality of personal care articles having a body facing surface and a garment facing surface; and a plurality of wrapper components each having an interior surface and an exterior surface, wherein each personal care article is disposed within the wrapper component. Each wrapper component has at least one absorbent personal care article contained within the wrapper component. The plurality of wrapping components with the absorbent articles disposed therein are disposed within the interior volume of the packaging component. A portion of the plurality of wrapper components contains a first wrapper component having at least a portion of a surface embossed and/or printed with a first wrapper pattern and/or having a portion of the first wrapper component cut or folded in a first wrapper pattern. Another portion of the plurality of wrapper components contains a second wrapper component having at least a portion of a surface embossed and/or printed with a second wrapper pattern and/or having a portion of the second wrapper component cut or folded in a second wrapper pattern. The first wrapper pattern and said second wrapper pattern are different from each other in at least one aspect. Further, a portion of the plurality of wrapper components may also contain additional wrapper components which have other patterns embossed and/or printed on a surface of the wrapper component and/or folded and/or cut into the additional wrapper components. In one aspect of the present invention, there are more than two different embossing patterns printing patterns, folding patterns and/or cutting pattern on the wrapper components within the package of the present invention. In the broadest aspect of the present invention, every wrapper component within a given package may have a different pattern embossed or printed thereon, and the printing or embossing is visible on the exterior surface.

In third aspect of the present invention, the first and second aspects of the present invention are combined where the plurality of absorbent articles and a plurality of wrapper components are contained in a package component. A portion of the plurality of the absorbent personal care articles in the packaging component are first absorbent articles having a first pattern embossed or printed on at least a portion of one of the surfaces. In addition, a portion of the plurality of the absorbent personal care articles in the packaging component are second absorbent articles having a second pattern is embossed or printed on at least a portion of one of the surfaces. A portion of the plurality of wrapper components contains a first wrapper component having at least a portion of a surface embossed and/or printed with a first wrapper pattern and/or having a portion of the first wrapper component cut or folded in a first wrapper pattern. Another portion of the plurality of wrapper components contains a second wrapper component having at least a portion of a surface embossed and/or printed with a second wrapper pattern and/or having a portion of the second wrapper component cut or folded in a second wrapper pattern. The first and second patterns embossed or printed on the absorbent personal care articles are different from each other in at least one aspect. Likewise, the first wrapper pattern and said second wrapper pattern are different from each other in at least one aspect.

In another aspect of the present invention, the present invention also provides a method of imparting different embossing patterns to a plurality of articles within a given package. The method contains the steps of providing a plurality of articles for embossing to an embossing roll, and embossing each of the articles with the embossing roll, wherein the embossing roll has a plurality of different embossing patterns thereon.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "personal care product" or "personal care article" as used herein refers to any article used to control bodily fluids, and includes "absorbent products," which refers to any article configured to absorb and retain bodily exudates, including urine, bowel movements, blood and menses, and includes such a product in a packaged and unpackaged configuration. As such, personal care products, as used herein, includes without limitation diapers, child toilet training pants, adult incontinence garments, male incontinence products, tampons, vaginal suppositories, pantiliners, pads, sanitary napkins, tissues, wipes, etc. Examples of commercially available personal care products include, without limitation, Poise® feminine care products, including pantiliners and pads, and Kotex® feminine care products, including pads, tampons and liners, all available from Kimberly-Clark Corporation, Neenah, Wis.

As used herein, the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbonded web" refers to a web of small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblown web" means a web of fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which may be continuous or discontinuous and are generally smaller than 10 microns in average diameter.

As used herein, the term "coform material" or "coform" generally refers to composite materials comprising a stabilized matrix of thermoplastic fibers and a second non-thermoplastic material. As an example, coform materials may be made by a process in which at least one meltblown die head is arranged near a chute through which pulp and/or other absorbent materials are added to the web while it is forming. Suitable absorbents include, but are not limited to, fibrous organic materials such as woody or non-woody pulp such as cotton, rayon, recycled paper, wood pulp fluff, cellulose and/or cellulosic staple fibers, and also include inorganic absorbent materials such as superabsorbent materials and/or treated polymeric staple fibers. Exemplary coform materials are disclosed in commonly assigned U.S. Pat. No. 5,284,703 to Everhart et al., U.S. Pat. No. 5,350,624 to Georger et al., and U.S. Pat. No. 4,100,324 to Anderson et al.; the entire contents of each of the aforesaid references are incorporated herein by reference.

As used herein, "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

"Airlaying" or "airlaid web" is a well known process by which a fibrous nonwoven layer can be formed. In the airlaying process, bundles of small fibers are separated and entrained in an air supply and then deposited onto a forming screen, usually with the assistance of a vacuum supply. The randomly deposited fibers then are bonded to one another using, for example, hot air or a spray adhesive.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein, "body-facing surface" means that surface of the article or component which is intended to be disposed toward or placed adjacent to the body of the wearer during ordinary use, while the "garment-facing surface" is on the opposite side, and is intended to be disposed to face away from the wearer's body during ordinary use. The outward surface may be arranged to face toward or placed adjacent to the wearer's undergarments when the absorbent article is worn.

As used herein, the term "pattern" refers to images or designs that are constituted by a figure (i.e., a lines, a symbol or character and the like). A pattern desirably has an aesthetic image or design that can provide certain benefits when the absorbent article is viewed by users or consumers of the absorbent articles.

As used herein, the term "different pattern" is intended to mean that there is at least one aspect of the pattern which is different. A different pattern can include, for example, objects which are not the same, colors which are not the same, a change in the spatial orientation of objects of the pattern, or other aspects which make it apparent to the user that the patterns are different. Minor variations created in a pattern due to normal process conditions variations are not included in this definition.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

DETAILED DESCRIPTION OF THE INVENTION

Personal care articles such as, for example, feminine care and incontinent absorbent products, generally include a liquid pervious topsheet, a substantially liquid impervious backsheet, and an absorbent core positioned and held between the topsheet and the backsheet. The topsheet is generally operatively permeable to the liquids that are intended to be held or stored by the absorbent article, and the backsheet may be substantially impermeable or otherwise operatively impermeable to the liquids intended to be held or stored. Disposable absorbent articles may also include other optional components or layers, such as liquid wicking layers, liquid distribution layers, barrier layers, and the like, as well as combinations thereof, which may improve the fluid handling and storage properties of the disposable absorbent article. Generally, disposable absorbent articles and the components thereof provide a body-facing surface and a garment-facing surface. The body facing surface is generally the topsheet and garment facing surface is the backsheet. As an alternative, the substantially liquid impervious backsheet may be replaced with a liquid pervious backsheet, when the absorbent personal care product is used in conjunction with another liquid impervious layer or article, such as, for example liquid impervious pants.

Figure 1:
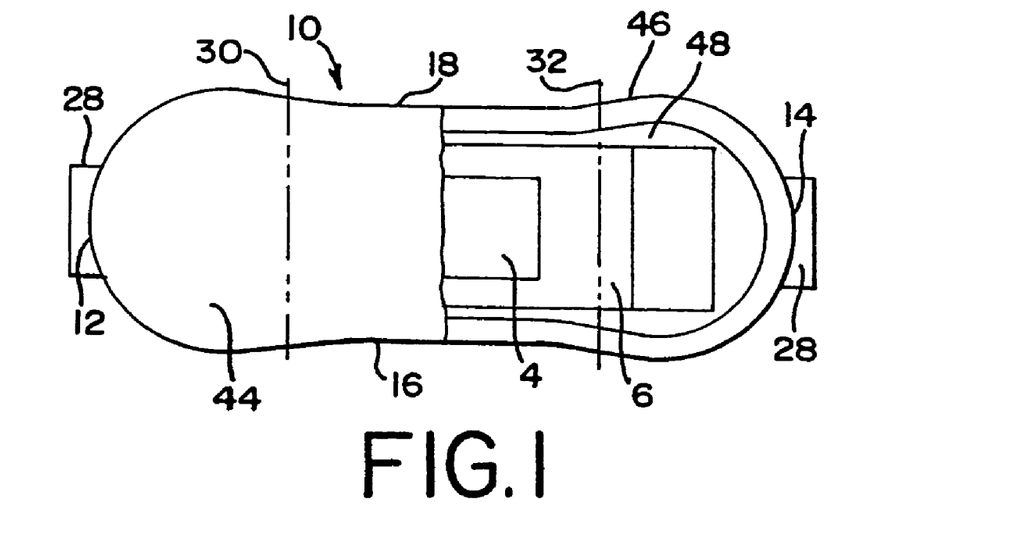
FIG. 1 is a body-side plan view of an exemplary personal care product component with a portion thereof partially cut away.
Figure 2:
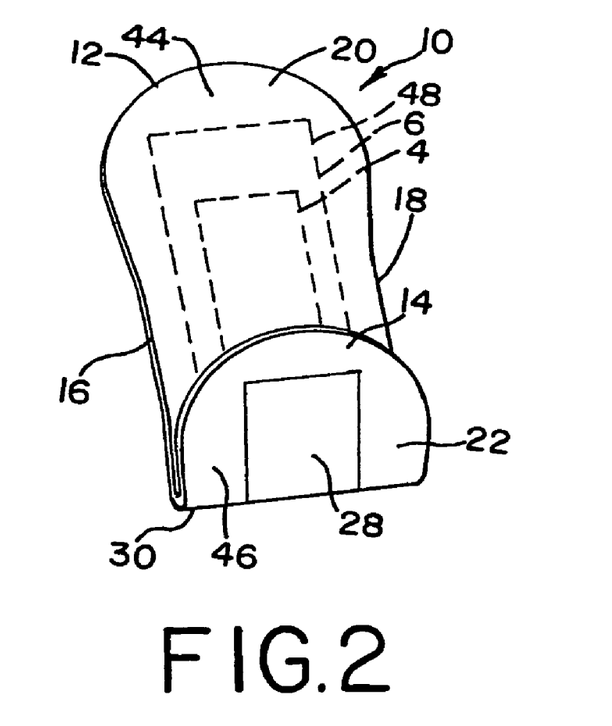
FIG. 2 is a perspective view of a product component in a partially folded configuration.

To obtain a better understanding of the absorbent articles which may be present in the packaging component of the present invention, attention is directed to FIGS. 1 and 2. In FIG. 1, an exemplary absorbent product 10 is shown as including an outer cover 46 (otherwise referred to as a baffle or backsheet), an absorbent core 48, an optional tissue layer 6, an optional distribution layer (surge layer) 4 and a body side liner 44 (also referred to as the top sheet). The absorbent product 10 also has a first side 16 and a second side 18. The first and second sides 16, 18, respectively, are the longitudinal sides of the elongated absorbent product. The sides can be contoured, for example in a concave shape, or they can be linear. The sides can further include flaps (not shown) that extend laterally outward. Flaps are known in the art and are shown in, for example U.S. Pat. No. 6,387,084 issued to VanGompel et al, which is hereby incorporated by reference in its entirety. In one embodiment (not shown), one or more elastic elements are disposed along the sides to form a gasket with the body of the user. Elastic sides are known in the art, as is shown in U.S. Pat. No. 6,315,765 issued to Datta et al., which is hereby incorporated by reference in its entirety. In one embodiment, the elastic elements are disposed between the liner and the outer cover.

The absorbent product 10 has a first body side surface 20 and a second garment side surface 22. Applied to at least a portion of the second garment side surface 22 is a garment attachment adhesive. In various embodiments, the garment attachment adhesive is configured as a single band of adhesive or as two or more spaced apart strips. Alternatively, the garment attachment adhesive includes a swirl pattern of adhesive which encompasses a major portion of the second garment surface 22 of the absorbent article 10.

A release strip 28, also known as a releasable peel strip, is removably secured to the garment attachment adhesive and serves to prevent premature contamination of the adhesive before the absorbent article 10 is secured to the crotch portion of an undergarment. In various embodiments, the garment attachment adhesive is designed to be secured to the inner crotch portion of an undergarment so as to keep the absorbent product in register with the body of the user. The release strip 28 may extend beyond one or both of the ends 12, 14 of the outer cover, as shown in FIG. 1. Alternatively, the release strip may be as short as the length of the garment attachment adhesive, or slightly longer than the adhesive or may be only as long as the garment attachment adhesive, but does not extend beyond the ends 12 and 14 of the outer cover, as shown in FIG. 2.

The body side liner or topsheet 44, which is preferably liquid permeable, may be formed from one or more materials. The body side liner or topsheet 44 must be able to manage different body excretions depending on the type of product. In feminine care products, often the body side liner or body contacting layer must be able to handle menses and urine. In the present invention, the body side liner or topsheet 44 may include a layer constructed of any operative material, and may be a composite material. For example, the body side liner or body contacting layer can include a woven fabric, a nonwoven fabric, a polymer film, a film-nonwoven fabric laminate or the like, as well as combinations thereof. Examples of a nonwoven fabric useable in the body side liner or topsheet 44 include, for example, an airlaid nonwoven web, spunbond nonwoven web, meltblown nonwoven web, a bonded-carded-web, hydroentangled nonwoven webs, spunlace webs or the like, as well as combinations thereof. Other examples of suitable materials for constructing the body side liner or topsheet 44 can include rayon, bonded carded webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat bondable materials.

Other examples of suitable materials for the body liner or topsheet 44 are composite materials of a polymer and a nonwoven fabric material. The composite materials are typically in the form of integral sheets generally formed by the extrusion of a polymer onto a nonwoven web, such as a spunbond material. In a desired arrangement, the liner or body contacting layer 44 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 48). The selected arrangement of liquid-permeability is desirably present at least on an operative portion of the body side liner or topsheet 44 that is appointed for placement on the body-side of the article. The body side liner or topsheet 44 can provide comfort and conformability, and can function to direct bodily exudates away from the body and toward the absorbent core 48. The body side liner or topsheet 44 can be configured to retain little or no liquid in its structure, and can be configured to provide a relatively comfortable and non-irritating surface next to the body-tissues of a wearer.

The baffle or backsheet 46 may include a layer constructed of any operative material, and may or may not have a selected level of liquid-permeability or liquid-impermeability, as desired. In a particular configuration, the baffle or backsheet 46 may be configured to provide an operatively liquid-impermeable baffle structure. The baffle or backsheet 46 may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the baffle or backsheet 46 can operatively permit a sufficient passage of air and moisture vapor out of the article, particularly out of an absorbent (e.g. storage or absorbent core 48) while blocking the passage of bodily liquids. An example of a suitable baffle material can include a breathable, microporous film, such as those described in, for example U.S. Pat. No. 6,045,900 to McCormack et al.

Bicomponent films or other multi-component films can also be used, as well as woven and/or nonwoven fabrics which have been treated to render them operatively liquid-impermeable. Another suitable baffle material can include a closed cell polyolefin foam. For example, a closed cell polyethylene foam may be employed.

The liquid permeable body side liner 44 and the liquid-impermeable baffle 46 may peripherally sealed together to enclose the absorbent core 48 to form the absorbent article 10. Alternatively, the body side liner or topsheet 44 can be wrapped around both the absorbent 48 and the baffle or backsheet 46 to form a wrapped pad. The body side liner 44 and baffle 46, and other components of the absorbent product, can be joined for example with adhesive bonds, sonic bonds, thermal bonds, pinning, stitching or any other attachment techniques known in the art, as well as combinations thereof.

The absorbent core 48 is designed to absorb body exudates, including menstrual fluid, blood, urine, and other body fluids. The absorbent core 48 may contain one or more layers of absorbent material. The layers can contain similar materials or different materials. Suitable materials for the absorbent core 48 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has good absorbency.

The absorbent core 48 can also be formed from a composite comprised of a hydrophilic material which may be formed from various natural or synthetic fibers, wood pulp fibers, regenerated cellulose or cotton fibers, or a blend of pulp and other fibers. A desired material is an airlaid material.

In one embodiment, the absorbent core 48 also includes a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Additional layers or substrates, including for example, the liquid acquisition and distribution layer 4, also referred to as a surge or transfer layer, and an optional tissue layer 6 are also incorporated into the absorbent product, for example between the body side liner or topsheet 44 and the absorbent core 48. The distribution layer 4 may be shorter than the absorbent core 48 or have the same length as the absorbent core 48. The distribution layer serves to temporarily hold an insulting fluid to allow the absorbent core sufficient time to absorb the fluid, especially when a superabsorbent material is present. In one embodiment, the absorbent core, transfer layer and other components, such as tissue layers, are free floating (unattached) between the outer cover and the liner, which are secured along only the peripheral edges thereof. Alternatively, the absorbent core, transfer layer and other components are attached to one or both of the outer cover and liner and/or to each other.

Figure 3:
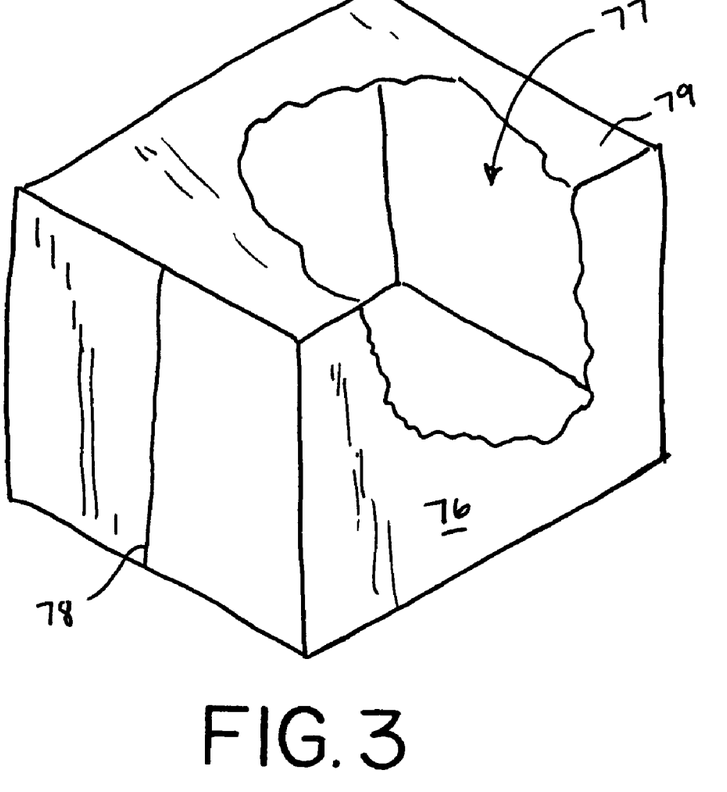
FIG. 3 is a perspective view of an outer packaging component configured to hold a plurality of product components with a portion thereof partially cut away.

Referring to FIG. 3, a plurality of absorbent articles 10, are packaged in a bulk packaging component 76, meaning a component capable of holding two or more absorbent articles. The package or packaging component 76 of the present invention containing the personal care articles can be formed from any material and can be any structure known in the art. Described in its simplest terms, the packaging component 76 must have an outer surface 79 which defines an interior volume 77 suitable for holding the absorbent personal care articles The plurality of absorbent articles 10 whether wrapped (discussed in more detail below) or unwrapped, are placed within the interior volume 77 of the packaging component 76. In one embodiment, the packaging component is formed as a bag having at least one side seal 78 securing a pair of edges of the bag together. In other embodiments, the plurality of absorbent articles is packaged in a box or carton. The bags may be prepared from a non-woven material, polymer film, paper, laminate, and/or cloth (including woven) materials, and combinations thereof. Boxes or cartons may be prepared from materials such as cardboard, paperboard, heavy weight paper and the like. Other packaging configurations include flexible packaging such flexible bags. Generally, flexible bags are formed from a thin material, such as paper, plastic, or a laminate of two or more of these materials. Suitable materials can be made from polymeric materials such as polyethylene, polypropylene, polyester, nylon, and the like, as well as any combination thereof. In one embodiment, the material is a low density polyethylene (LDPE) film. In another embodiment, the material is a LDPE/LLDPE (linear low density polyethylene) film laminate. In yet another embodiment, the material is a LDPE/MDPE (medium density polyethylene) film laminate, a LDPE/HDPE (high density polyethylene) film laminate or the like. In another embodiment a polyethylene/polypropylene combination is used. In a specific embodiment, the material is a polyethylene film or film laminate having a thickness of about between about 1 and 5 mils (about 0.025 to 0.125 mm). In addition, the packaging component may have other items not specifically shown, such as opening devices, handles and the like, or could have other shapes besides the parallelepiped, such as circular, oval, freeform and the like without departing from the spirit and scope of the present invention. The configuration of the packaging component is not critical to the present invention, so long as the packaging component has a large enough interior volume to hold at least two personal care articles.

In the present invention, the topsheet or body facing surface of each absorbent article may be embossed, printed or otherwise imparted with a pattern. The absorbent articles of the present invention are placed in a package component and there are at least two absorbent articles, each having different patterns embossed or printed on the body-facing surface within a given package. In an alternative embodiment, the garment facing layer may be embossed or printed with a pattern. In the case of incontinence pads, feminine napkins and pantiliners, the garment facing surface may also be printed with a pattern. Again, the feature of the present invention is that there are at least two different absorbent articles each having different patterns embossed or printed on the garment facing side of each absorbent article.

The absorbent articles of the present invention may be placed into the interior volume of the packaging component without being further wrapped in an additional component. In the alternative, the absorbent articles may be wrapped in a wrapper component. The wrapper component may have a number of different configurations without departing from the scope of the present invention.

Figure 4:
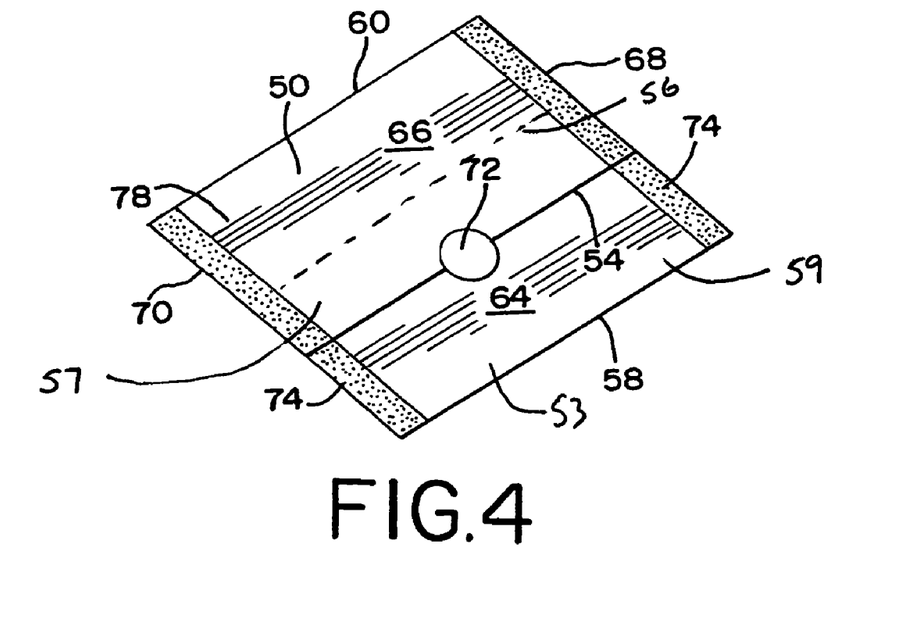
FIG. 4 is perspective view of an embodiment of an individual wrapper component.
Figure 5:
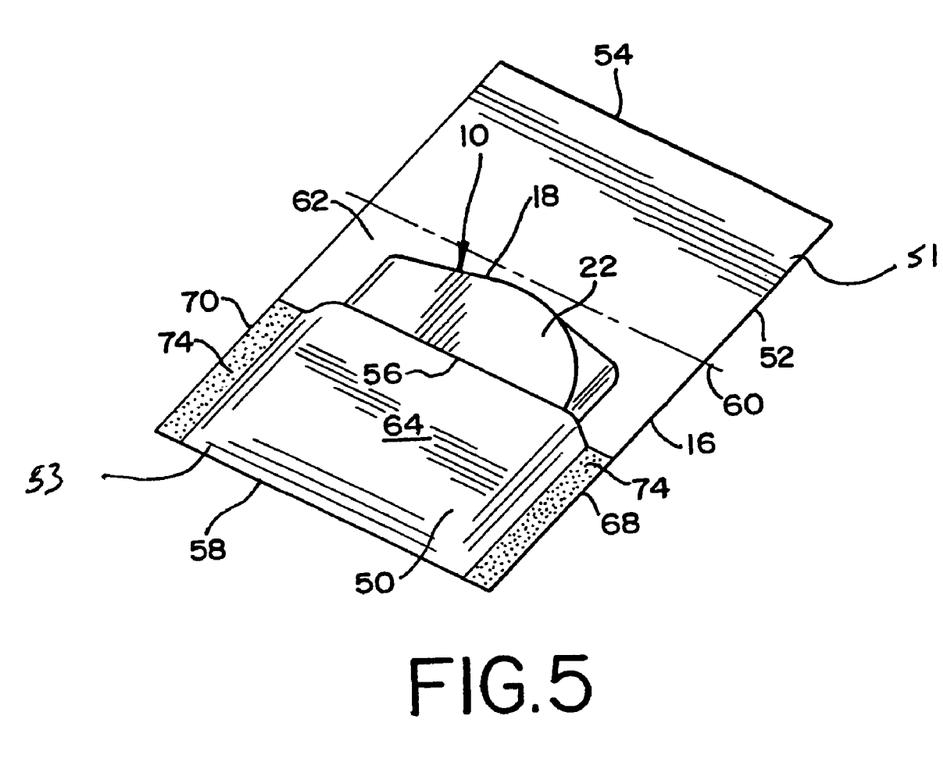
FIG. 5 is a perspective view of an individual packaging component in an open configuration with an absorbent product component in a folded configuration.

Although the wrapper component may have different configurations or can be prepared in other ways without departing from the scope of the present invention, referring to FIGS. 4 and 5, a typical wrapper component has a pouch 50 formed from a strip or web 52 of material having a first and second ends having free edge 56, 54, respectively. It should be understood that the term "free edge" refers to an edge that is unattached after the wrapper component is opened, regardless of whether the free edge is attached when the wrapper component is closed. Each of the first and second ends is folded along fold lines to define the top 60 and bottom edge 58 of the pouch 50, respectively. The folded pouch has a back panel 62, a first panel 64 and a second panel 66. The first panel 64 and back panel 62 may be secured along side edges 68, 70 thereof to form a pocket shape to receive the absorbent product. Each wrapper has an interior surface 51 and an exterior surface 53. In one embodiment, the pocket and pouch may be shaped and dimensioned to receive a single product component, which is individually wrapped in the pouch. Alternatively, the pocket and pouch may be configured to hold more that one absorbent article. The second panel 66 is folded over the first panel 64 such that the free edge 54 of the second panel overlies the first panel 64. The first panel 64 has a covered or overlap portion 57 extending between the free edge 54 (exterior) and the free edge 56 (interior), which covered or overlapped portion 57 underlies the second panel 66. Generally, the second panel may be a flap, but it is not required for the present invention that the second panel be a flap. A flap is a piece of the wrapper component which may be manipulated by a user by grasping and the end of the second panel and pulling the second panel upward, towards the top 60.

As an alternative to having the free edge overlap the first panel, the wrapper component can be designed such that there is no overlap between the free edge 54 and the first panel 64, without departing from the scope of the present invention. For example, the free edges 54, 56 may abut each other (not shown) or may be separated by a small distance (also not shown). As such, in this alternative, the second panel is defined merely as another panel.

When the second panel overlaps the first panel, in one example, the portion 57 has a length of about 0 about 50 mm, generally about 2-22 mm and typically about 4-10 mm between the free edges 54, 56. In various embodiments, the overlap distance is less than or equal to about 95% of the overall packaging component length in a closed configuration, more desirable less than or equal to about 35% of the packaging component length, and more desirably less than or equal to about 20% of the packaging component length. In various embodiments, the free edge 54 is positioned a distance from either edge 58, 60 that is greater than or equal to about 10% of the overall length of the packaging component (in a closed configuration), more desirably greater than or equal to about 30%, and more desirably about 50% of the packaging component length. The first panel further includes an uncovered second portion 59 extending between the free edge 54 and the bottom edge 58. Of course, it should be understood that the length and width of the article and packaging components can vary according to the type of article and the size of the article.

A pair of side seals 74 secures the first panel 64 to the back panel 62. The side seals are desirably formed after the first panel is folded over the back panel and the second panel is folded over the back panel and the first panel. Although, it is possible that the first panel could first be sealed to the back panel, and the second panel then sealed to one or both of the back panel and first panel. In an alternative configuration, the second panel is not sealed at the side edges of the first panel and back panel. This embodiment is described in more detail below. The sides may be sealed by any method known to those skilled in the art. Exemplary sealing methods include, for example, adhesive sealing, bonding by the application of heat and pressure, ultrasonic bonding or any other art known bonding methods. In one embodiment of the present invention, the side seals 74 may be frangible, meaning they can be easily broken such that the second panel 66 can be separated from the first panel 64 and back panel 62, and such that the first panel 64 can be easily separated from the back panel 62, wherein the product component 10 is exposed for removal from the pouch by the user.

In an alternative configuration, one or more free edges may be formed along a perforation line, which is or may be adhered to an underlying layer, with the edge defined by the perforation line being a "free edge" after the perforation line is broken. The free edge can be a single layer cut or formed edge, or can include a double-layer folded edge, or can include an edge formed by a plurality of layers. The wrapper material can be formed from materials, such as, but not limited to, a non-woven material, films, paper, laminates, and/or cloth (including woven) materials, and combinations thereof. For example, the pouch can be made as disclosed in U.S. Pat. No. 6,716,203, to Sorebo et al., the entire disclosure of which is hereby incorporated herein by reference. Suitable laminates useable in the present invention include, spunbond-spunbond laminate (SS), spunbond-meltblown-spunbond laminates (SMS), spunbond-film laminates (SF), and film-film laminates. In one embodiment, the pouch is made of a film/spunbond laminate material available from Kimberly-Clark Corp, and known as HBSTL ("highly breathable stretch thermal laminate"), and which material is further disclosed in U.S. Pat. No. 6,276,032, to Nortman et al., the entire disclosure of which is hereby incorporated herein by reference.

In one alternative embodiment, the second panel 66 is releasably secured to the first panel 64. For example, a fastening element 72, shown as a tab in FIG. 4, is secured across the free edge 54 of the second panel 66 to secure the second panel 66 to the first panel 64. The fastening element can be releasably secured to both of the second panel and first panel, or it can be fixedly secured to one of the second panel and first panel and releasably secured to the other. Other possible configuration include that the fastening element is fixedly secured to both panels and one or both of the panels is provided with an area of weakness, such as a perforated area, which allows a portion of one or both of the panels to be removed or damaged when the wrapper is opened. The fastening element can be formed as adhesive tape, a snap, a button, a mechanical fastener (e.g., hook and loop), a tie, or as any other device known by those skilled in the art. The fastening element can have various alternative shapes, including but not limited to a square, rectangle, triangle, circle, oval, obround, oblong or diamond shape, or any other irregular shape or pattern. In an alternative embodiment, the fastening element is formed on the inside of the second panel such that it engages the first panel as the second panel is folded thereover and is not visible to the user. For example, the fastening of the second panel 66 to the first panel 64 may be accomplished by the use of an adhesive applied to the side of the second panel 66 which contacts the first panel 64, to the side of the first panel 64 which contacts the second panel 66, or both. This adhesive may be applied as a ribbon, dot, a swirl pattern or any other pattern which effectively adheres the second panel 66 to the first panel 64. In another alternative way to fasten the second panel 66 to the first panel 64, the second panel 66 is simply sealed to the first panel 64 with a heat seal or other weld, with the weld defining the fastening element. In another embodiment, the second panel 66 is not sealed or otherwise attached to the first panel 64, but rather is simply folded thereover. Alternatively, the sides of the second panel are sealed to the back panel and to the first panel, with the side seals being breakable in response to a user grasping and lifting the second panel. It is within the scope of the present invention that the sensory cue could be located on the fastening element.

In some embodiments, the second panel 66 is refastenably secured to the first panel 64, while in others, the second panel 66 is not intended to be secured to the first panel 64 once the wrapper component is opened. For example, in one embodiment, the free edge 54 is defined by a perforation line, with the second panel not being refastenable after the perforation is broken.

Referring to FIG. 5 the wrapper component is shown. In FIG. 5, the absorbent product 10 is shown in the wrapper component in a folded configuration. For example, the absorbent product can be folded along a pair of fold lines 30, 32 to form a tri-fold configuration. In other embodiments, the absorbent product can be bi-folded, flat or rolled. The absorbent product is then inserted into an individual wrapper component, otherwise referred to as a wrapper or pouch. Alternatively, a plurality (meaning two or more) of products 10 can be disposed in a wrapper component. One product/wrapper configuration is shown in U.S. Pat. No. 6,601,706 to McManus et al., which is hereby incorporated by reference. Other wrapper/absorbent product configurations are described in, for example U.S. Patent Application Publication 2002/0079246 to Ling et al., which is hereby incorporated by reference. The absorbent products can be oriented in various ways within the individual wrapper component, for example, with the fold lines 30, 32 running parallel or perpendicular to the sides of the wrapper component 68, 70.

Figure 6A:
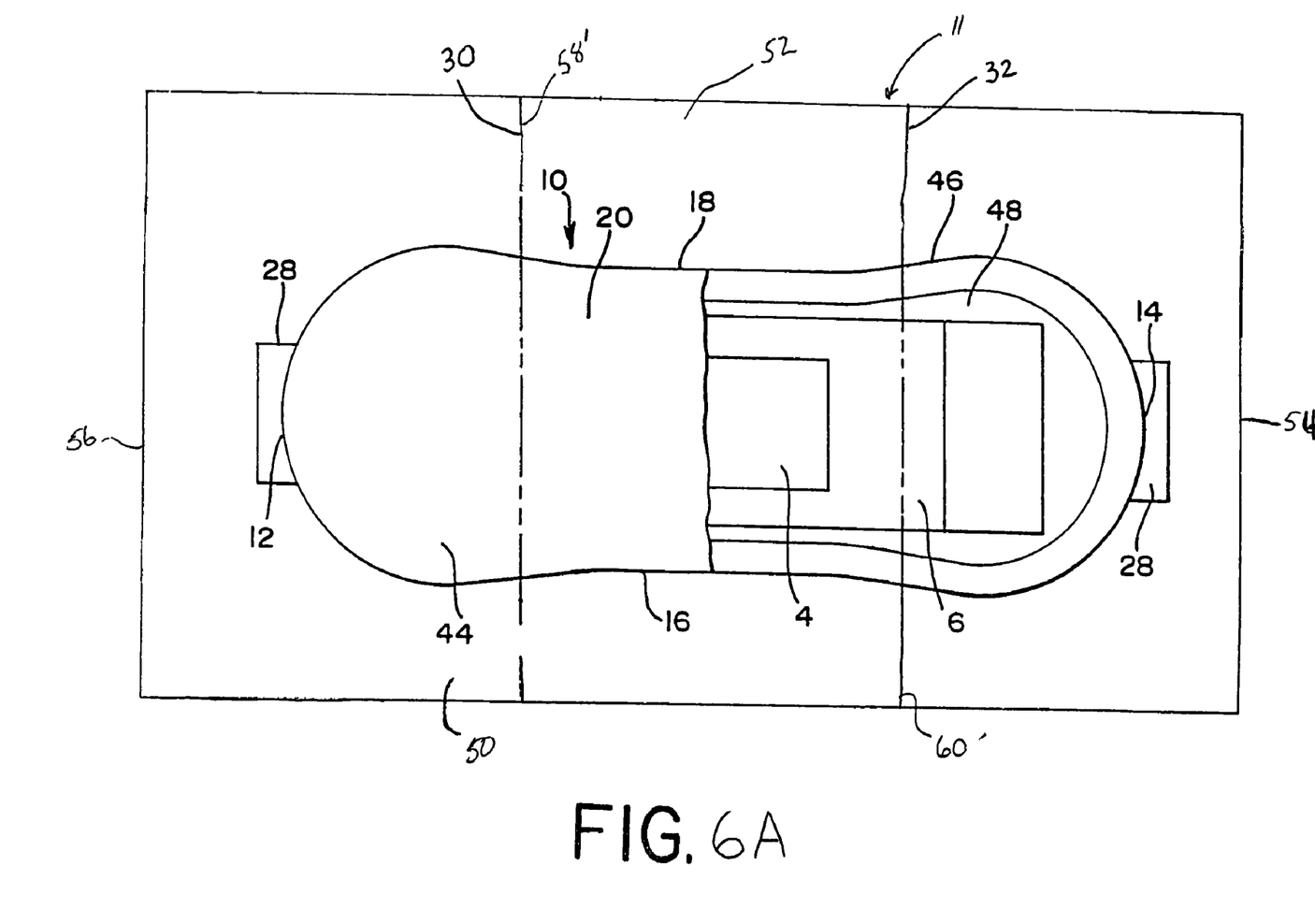
FIG. 6A is a plan view of another wrapper component in an open configuration with a personal care product component in an unfolded configuration.
Figure 6B:
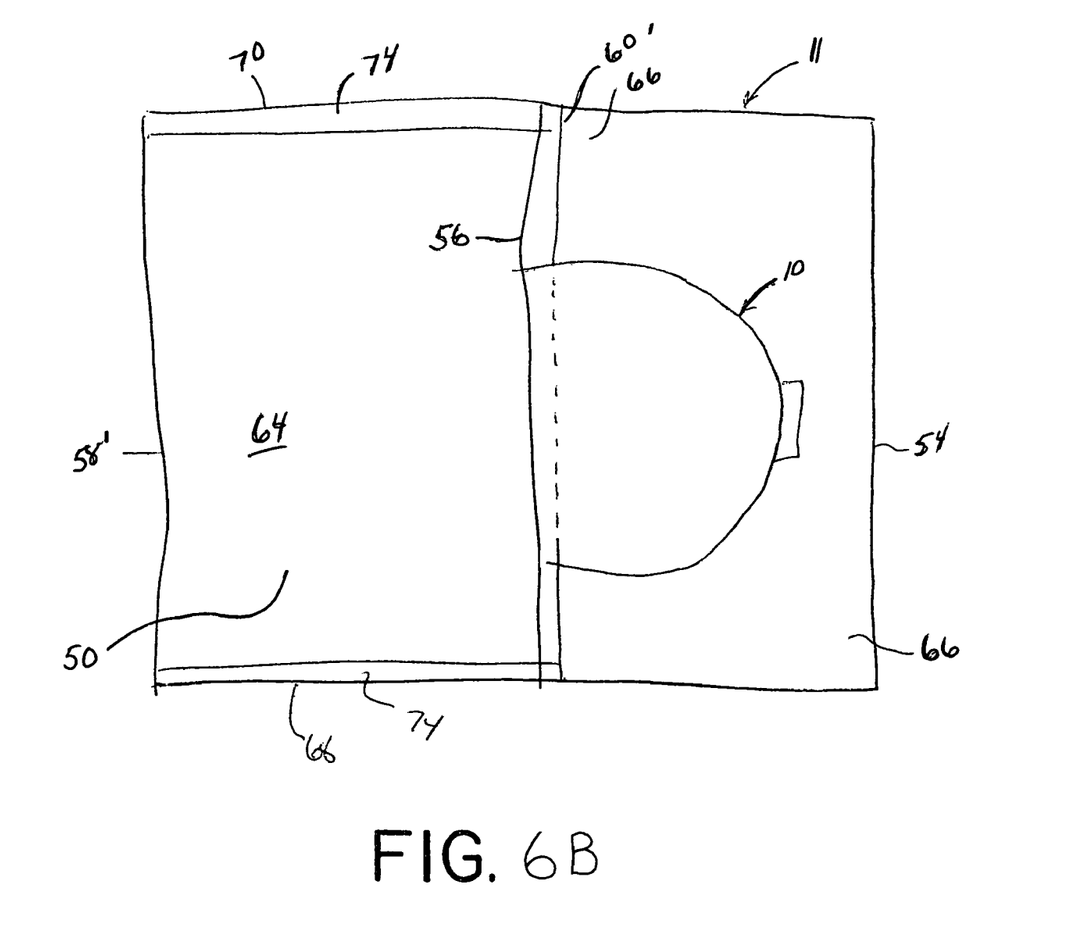
FIG. 6B is a perspective view of the wrapper component in a partially open configuration with the personal care product component in a partially folded configuration.

In the present invention, the wrapper component may be preformed or folded with the absorbent article contained in the strip of material used to prepare the wrapper component. As is shown in FIGS. 6A and 6B, the wrapper component is a strip or web 52 of material having a first and second ends having free edge 54, 56, respectively. First, the wrapper component and the absorbent article are folded together along line 30 such that the body side liner or topsheet 44 of the absorbent article comes in contact with itself. In addition, each of sides 68 and 70 come into contact with itself and may be sealed together to form two side seals 74, as is shown in FIG. 6B, or can remain unsealed at this stage. Generally, the wrapper component sides are bonded in the side regions 68 and 70. The sides may be sealed by any method known to those skilled in the art including adhesive sealing, bonding by the application of heat and pressure, ultrasonic bonding or any other art known bonding methods. When folded and sealed as shown in FIG. 6B, the wrapper component has a pouch with a back panel 62, a first panel 64 and a second panel 66. The second panel 66 is then folded over the first panel 64 along line 32 such that the free edge 54 of the second panel overlies the first panel 64. In this configuration, the portion of the top sheet of the absorbent article will be in contact with the first panel 64 of the wrapper component. As with the above described configuration, the first panel 64 has a covered or overlapped portion 57, shown in FIG. 4, extending between the free edge 54 (exterior) and the free edge 56 (interior), wherein the covered or overlapped portion 57 underlies the second panel. It may be advantageous from a materials standpoint to fold the wrapper component and the absorbent article together, since the release strip 28 may be unnecessary since the wrapper component could also be used as the release strip. As with the previous described configurations, the wrapper component may be designed such that there is no overlap between the free edge 54 and the first panel 64, without departing from the scope of the present invention. For example, the free edges 54, 56 may abut each other or may be spread apart by a small distance (not shown). As such, in this alternative, the second panel is defined merely as another panel.

Other wrapper configurations, may also be used in the present invention, including those described in U.S. Pat. No. 6,036,679 to Balzar et al, which is hereby incorporated by reference. Another possible wrapper configuration, the wrapper component is formed as a portion of the product component. For example, an outer cover, such as the baffle material, can form a wrapper component, as shown for example in U.S. Pat. No. 5,993,430 to Gossens, which is hereby incorporated herein by reference. It should be understood that in these embodiments, the product component is considered to be disposed in the wrapper component when the wrapper element is sealed or otherwise closed. In other embodiments, the product component is rolled, with a second panel or first panel portion of a wrapper component overlying a panel portion of the wrapper component, regardless of whether the wrapper component is integral with the product component or separate therefrom.

Figure 7:
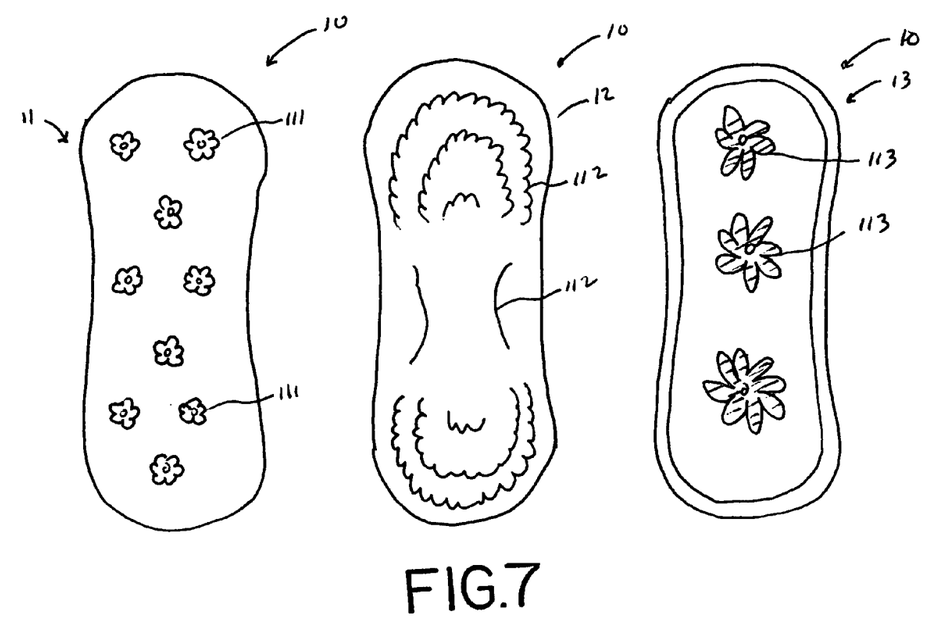
FIG. 7 is a plan view of absorbent articles with different patterns.

In one aspect of the present invention, as shown in FIG. 3, a packaging component 76 having an outer surface 79 and an interior volume 77 contains within the interior volume a plurality of absorbent personal care articles 10. Each absorbent personal care article 10 has a garment facing surface 46 and a body facing surface 44. A portion of the plurality of the absorbent personal care articles 10 in the packaging component are first absorbent articles 11 having a first pattern 111 embossed or printed on at least a portion of one of the surfaces. The surface may be either the body facing surface or the garment facing surface. In addition, a portion of the plurality of the absorbent personal care articles in the packaging component are second absorbent articles 12 having a second pattern 112 that is embossed or printed on at least a portion of one of the surfaces. In this aspect of the present invention, the first 111 and second 112 patterns are different from each one another in at least one aspect. As shown in FIG. 7, the first pattern has flowers and the second pattern has a cloud-like design. Further, a portion of the plurality of absorbent personal care articles may also contain additional absorbent articles 13 which have yet another pattern 113 embossed or printed on one of the surfaces. Desirably, there are more that two different embossing or printing patterns on the absorbent articles within the package of the present invention. Generally, in the present invention every absorbent article 10 within a given package 76 may have a different pattern embossed or printed on the body facing surface or the garment facing surface of each of the absorbent articles. Typically, there will be between about 2 and about 20 different embossing patterns within a given package. Generally, it is desired that the embossing or printing is on the body facing side of the absorbent article.

Figure 8:
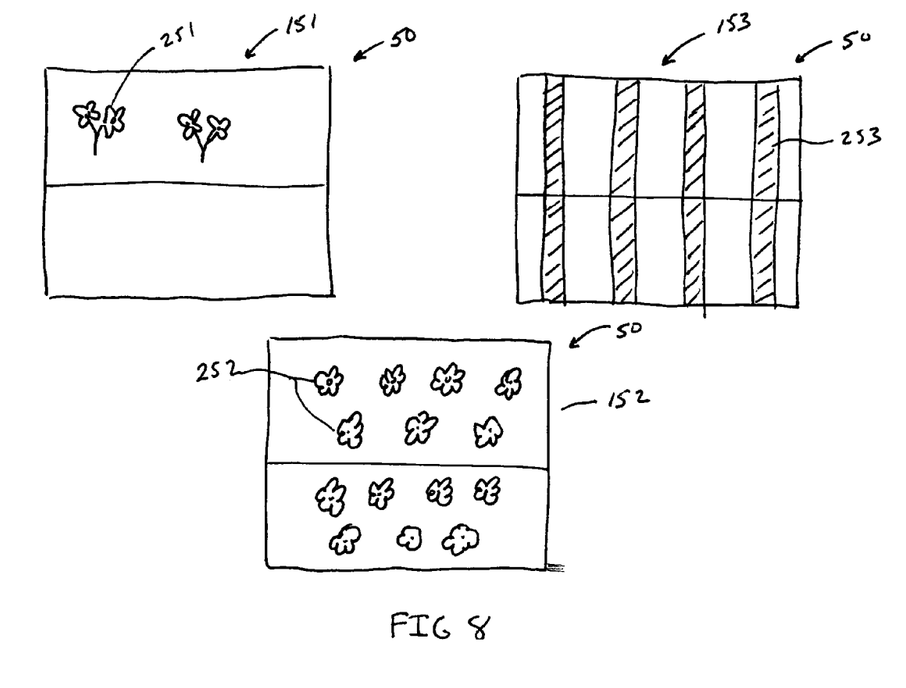
FIG. 8 is a plan view of wrappers with different patterns.

In another aspect of the present invention, personal care articles may be wrapped in a wrapper component. In this aspect of the present invention, there is a plurality of wrapper components 50, each having an interior surface 51 and an exterior surface 53. A portion of the wrapper components within the interior volume of the package have at least a portion of a surface embossed or printed with a first wrapper pattern 251, and a portion of the plurality of wrapper components have a portion of a surface embossed or printed with a second wrapper pattern 252, as is shown in FIG. 8. The wrapper components may be divided into a first wrapper component 151 with a first wrapper pattern 251 and a second wrapper component 152 with its second wrapper pattern 252. Additionally, a portion of the wrapper components may be an additional wrapper component 153 with an additional wrapper pattern 253. It is noted that the typical wrapper component is made of a relatively lightweight material, embossing one surface of the wrapper material will usually result in the negative of the embossing pattern being raised on the other surface. The first wrapper pattern 251, second wrapper pattern 252 and any additional wrapper pattern 253 are all different from each other in at least one aspect. Desirably, there are more that two different embossing or printing patterns on the wrappers within the package of the present invention. Generally, in the present invention every wrapper component within a given package may have a different pattern embossed or printed on the exterior surface of the wrapper component. Typically, however, there will be between about 3 and about 20 different wrapper embossing or printing patterns within a given package.

In the alternative, or in addition to the embossed or printed wrapper pattern, wrapper patterns may be imparted into the wrapper by cutting or folding the wrapper components in different patterns. For example, the free edge of the flap in one wrapper component could be scalloped, while another wrapper component could have a sine-wave type edge. Further, the wrapper components could be folded in different ways to change the appearance of individual wrapper components.

It is pointed out that the patterns shown in FIGS. 7 and 8 are merely exemplary patterns and are not intended to limit the invention in any way.

In present invention, the plurality of absorbent personal care articles within a package may optionally be wrapped in wrapper components as described above. There may be one or more absorbent personal care articles within a given wrapper component. All of the wrapper components within a given package may be identical or may be different, as is described above, i.e. by having different embossing or printing patterns on a portion of a surface of the wrapper component. If different embossing or printing patterns are used for the wrapper components, as is shown in FIG. 8, the embossing or printing patterns for the plurality of absorbent articles may be optionally matched to the wrapper embossing or printing patterns, or may be different. As an example of matched patterns, the second wrapper pattern 252 shown in FIG. 8 is the same as the first pattern 111 shown in FIG. 7. In one aspect of the present invention, the embossing pattern on the first absorbent article is the same as the embossing or printing pattern on the first wrapper component. As a result, the wrapper component and the absorbent article would be coordinated with each other.

Embossing of the absorbent article or the wrapper component may be accomplished by any means know to those skilled in the art. Methods of embossing material are well known in the art. For example, the absorbent article or wrapper component material may be passed between a heated or unheated anvil roll and heated or unheated embossing roll, which is engraved with a relief embossing pattern. Other techniques known to those skilled in the art, including using ultrasonic embossing and the like may also be used to obtain the desired embossing effect. The method in which the wrapper component is embossed is not critical to the present invention. Generally, it is desired, but not required, that the embossing pattern used contain objects which impart a feminine flair to the wrapper component, such as floral designs, when the absorbent articles are designed for use in feminine personal care articles.

Embossing can be varied on the absorbent article or wrapper component. The embossing pattern can be registered or non-registered as well as a high density pattern or a low-density pattern. With respect to the wrapper component, from a standpoint of cost, the wrapper component is embossed as opposed to printed, since embossing is typically less expensive than printing.

In the embossed area, the corresponding material or materials of the article are operatively compressed and substantially permanently deformed along the z-directional thickness of the article or wrapper component. The corresponding material or materials in the embossment region are operatively molded to form a desired pattern. As is stated above, any manner such as by the application of heat, including hot calendar embossing or by ultrasonic means may be used to emboss the absorbent personal care articles or the wrapper components. Preferably, the absorbent personal care articles or the wrapper components of the present invention are embossed by passing the absorbent personal care articles or the wrapper components through the nip between a pair of embossing rolls, at least one of the rolls being heated. The total embossed area of the fabric is preferably from about 5% to about 30% of the surface area of the wrapper component or the absorbent personal care article. The absorbent personal care articles or the wrapper components have an embossed pattern of densified areas separated by high-loft regions, also as described above. When embossing rolls are used, the fabric can be embossed with very intricate patterns which are clearly visible in the absorbent personal care articles or the wrapper components. The temperature of the embossing rolls can vary depending on the polymers used, the polymer components of the fibers or filaments, the basis weight of the materials used to prepare the absorbent personal care articles or wrapper component, the line speed, and other factors, but it must be sufficient to cause cold fusion bonding between the fibers or filaments. The densified area which results from the embossing is usually from about 5 to about 30% of the surface area of a surface of absorbent personal care articles or the wrapper components. When the densified area is less than about 5%, the abrasion resistance of the absorbent personal care articles or the wrapper components may too low. When the densified area of the fabric is greater than about 30%, the absorbent personal care articles or the wrapper components tend to be too stiff. It is pointed out that in the present invention that embossing patterns having greater that about 30% surface area are within the scope to the present invention as are embossing of less than 5% of the surface area, but these embodiments are usually not desirable. High density embossing patterns are those patterns with greater than about 20% of the surface are being embossed and low density bonding pattern are bonding patterns with an embossing area of less than about 20% of the embossed surface's surface area.

In the present invention, the different embossing patterns on the absorbent personal care articles or the wrapper components may be imparted in many different ways, including using side-by-side production lines, a single production line with separate embossing sections, i.e. a single line splits into two or more lines to emboss the absorbent personal care articles or the wrapper components, using a single process line and preparing the absorbent personal care articles or the wrapper components in a batch process, changing the embossing roll after each batch of absorbent personal care articles or the wrapper components, or a single production line and using an embossing roll with a long repeat pattern. By a long repeat pattern, it is meant that several absorbent personal care articles or the wrapper components are embossed before the pattern repeats itself. This can be accomplished by using, for example, a large diameter embossing roll. Other types of embossing rolls, such as embossing rolls with several different patterns across the width of the roll may also be used. In using the variable pattern rolls, whether the large diameter roll with a long repeat pattern or the side-by-side pattern embossing roll, it is preferred, but not required that the embossing area of each embossing pattern be about the same as the other patterns of the roll. Generally, the embossing pattern area percentage should not vary by more that about 10% of the total area of the absorbent personal care articles or the wrapper components. Desirably, the variation should be less that about 5%. It is noted that this process may be used for prepare packages of other types of articles having different embossing patterns besides absorbent articles. The method used is not critical to the present invention; however, a batch process is not a desirable means if all of the absorbent personal care articles within a given package have the same absorbency. The batch process may be beneficial in producing products of different absorbencies in a single package.

In present invention, printing may also be used to impart a pattern to the wrapper component or a surface of the absorbent article. In case of the wrapper component, typically the printing will be placed on the exterior surface of the wrapper component. However, it is within the scope of the present invention to print the pattern on the interior surface of the wrapper component or between the layers of the wrapper component if more than one layer is present.

Any printing process known to those skilled in the art may be used in the present invention. Given that different patterns are on the wrapper component is required in one aspect of the present invention, desirably a printing system which can print patterns based on data stored in a memory device can be used. Examples of such printers include ink jet printing systems, digital off-set printing systems or color laser printing systems. In a typical operation, a controller, usually a computer selects the pattern to be printed from the memory device and sends to the printer the pattern to be printed. Optionally, but desirably if on an outer surface, once printed the printed portion is dried with a drier to fix the printing ink of the wrapper component. The controller may be set-up to print the stored patterns in a random fashion or in a particular order to ensure a variety in the package.

In the present invention, the printing may be accomplished in-line with the production of the absorbent articles or may be accomplished off-line. As with embossing each process has advantages and disadvantages.

The patterns printed or embossed on the articles or wrappers may be a variety of objects, characters, pictures and the like. The final use of the absorbent articles will determine the patterns used. For example for feminine care articles, items of a feminine flair, such as flowers and the like may be selected.

The patterns also may be used to distinguish articles within a given package to designate different absorbencies of the absorbent articles or different sizes of the absorbent articles. For example, absorbent articles with a low absorbency may be provided in the package in a wrapper with a first wrapper pattern or one of the surfaces of the absorbent article may be provided with a first pattern. Absorbent articles having a higher absorbency may be provided in the package in wrapper having a second wrapper pattern or one of the surfaces of the absorbent article may be provided with a second pattern. If the package has articles of different absorbencies, a card, information sheet or a portion of the outer surface of the package may be printed with information of how to determine the absorbency of a given absorbent article. An intuitive method may be used to signal to the consumer the absorbent performance of a given article. For example, if embossing is used, heavier embossing may be used to signify a higher absorbency. In addition, the different patterns may also be used to designate different scents of the different absorbent articles within a given package.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A package of absorbent personal care articles comprising
   a packaging component having an outer surface and an interior volume;
   a plurality of absorbent personal care articles having a liquid-impermeable garment facing surface and a liquid-permeable body facing surface disposed within the interior volume of the packaging component, and
   a plurality of wrapper components, each wrapper component comprises an interior surface and an exterior surface, wherein each wrapper component has a single absorbent article contained within the wrapper component,
   wherein a portion of the plurality of absorbent personal care articles comprises a first absorbent article comprising a first pattern embossed on at least a portion of one of the surfaces of the first absorbent article and a portion of the plurality of absorbent personal care articles comprises a second absorbent article comprising a second pattern embossed on at least a portion of one of the surfaces of the second absorbent article, wherein the first and second patterns are different from each other.

2. The package of absorbent personal care articles of claim 1, wherein a portion of the plurality of wrapper components comprises a first wrapper component comprising at least a portion of a surface embossed and/or printed with a first wrapper pattern and/or having a portion of the first wrapper component cut or folded in a first wrapper pattern and a portion of the plurality of wrapper components comprises a second wrapper component comprising at least a portion of a surface embossed and/or printed with a second wrapper pattern and/or having a portion of the second wrapper component cut or folded in a second wrapper pattern, said first wrapper pattern and said second wrapper pattern are different from each other.

3. The package of absorbent personal care articles of claim 2, wherein the first and second patterns on the absorbent articles comprise embossed patterns and the first and second wrapper patterns on the wrapper components comprise printed patterns.

4. The package of absorbent personal care articles of claim 3, wherein each wrapper comprises a first panel, a back panel and a second panel, said first panel is connected to said back panel and said second panel is connected to said back panel at an opposite end from where the first panel is connected to the back panel, said second panel having a free edge positioned adjacent said first panel, wherein at least a portion of the plurality of wrapper components comprises wrappers with at least one of the first panel and the second panel is embossed or printed with the first wrapper pattern or the second wrapper pattern.

5. The package of absorbent personal care articles of claim 4, wherein the first or second wrapper pattern are each embossed patterns.

6. The package of absorbent personal care articles of claim 4, wherein at least a portion of the second panels of the plurality of wrapper components comprise either the first wrapper pattern or the second wrapper pattern.

7. The package of absorbent personal care articles of claim 4, wherein at least a portion of the second panels and first panels of the plurality of wrapper components comprise either the first wrapper pattern or the second wrapper pattern.

8. The package of absorbent personal care articles of claim 2, wherein the first wrapper pattern and the second wrapper pattern are each embossed patterns, the first pattern embossed on the first absorbent article is the same as the first wrapper pattern and the second pattern embossed on the second absorbent article is the same as the second wrapper pattern.

9. The package of absorbent personal care articles of claim 8, wherein each first absorbent article is contained within a first wrapper component and each second absorbent article is contained within a second wrapper component.

10. The package of absorbent personal care articles of claim 1, wherein said first pattern is embossed on the body facing surface of first absorbent article and the second pattern is embossed on the body facing surface of second absorbent article.

11. The package of absorbent personal care articles of claim 10, wherein the first pattern comprises a high density embossing pattern.

12. The package of absorbent personal care articles of claim 11, wherein the second pattern comprises a low density embossing pattern.

13. The package of absorbent personal care articles of claim 11, wherein the second pattern comprises a high density embossing pattern.

14. The package of absorbent personal care articles of claim 10, wherein the first pattern comprises a low density embossing pattern.

15. The package of absorbent personal care articles of claim 14, wherein the second pattern comprises a low density embossing pattern.

16. The package of absorbent personal care articles of claim 1, wherein a least a portion of the plurality of absorbent articles further comprises at least one additional absorbent article comprising a body facing surface and a garment facing surface and having a different pattern embossed on at least one of the body facing surface or the garment facing surface of the additional absorbent article.

17. The package of absorbent personal care articles of claim 16, wherein the first absorbent article, the second absorbent article and the additional absorbent article each have a different absorbency from the other absorbent articles.

18. The package of absorbent personal care articles of claim 1, wherein the first absorbent article has a different absorbency than the second absorbent article or the first absorbent article has a different size than the second absorbent article.

19. The package of absorbent personal care articles of claim 1, wherein the first and second absorbent article is selected from the group consisting of sanitary napkins, pantiliners, incontinence pads and incontinence garments.

20. A package of absorbent personal care articles comprising
    packaging component having an outer surface and an interior volume;
    a plurality of absorbent personal care articles; and
    a plurality of wrapper components each having an interior surface and exterior surface,
    wherein each absorbent personal care article is disposed within a wrapper component, the plurality of wrapping components with the absorbent articles disposed therein are disposed within the interior volume of the packaging component; and wherein a portion of the plurality of wrapper components comprises a first wrapper component comprising at least a portion of a surface embossed with a first wrapper pattern and/or having a portion of the first wrapper component cut or folded in a first wrapper pattern and a portion of the plurality of wrapper components comprises a second wrapper component having at least a portion of a surface embossed with a second wrapper pattern and/or having a portion of the second wrapper component cut or folded in a second wrapper pattern, said first wrapper pattern and said second wrapper pattern are different from each other.

21. The package of absorbent personal care articles of claim 20, wherein each wrapper component comprises a first panel, a back panel and a second panel, said first panel is connected to said back panel and said second panel is connected to said back panel at an opposite end from where the first panel is connected to the back panel, said second panel having a free edge positioned adjacent said first panel, wherein at least of a portion of the plurality of wrapper components comprises wrappers with at least one of the first panel and the second panel is embossed with the first wrapper pattern or the second wrapper pattern.

22. The package of absorbent personal care articles of claim 20, wherein the first and second wrapper patterns are each located on at least the second panel of the wrapper component.

23. The package of absorbent personal care articles of claim 20, wherein the first and second wrapper patterns are each located on both the second panel and the first panel of each wrapper component.

24. The package of absorbent personal care articles of claim 20, wherein a portion of the plurality of wrapper components comprises at least one additional wrapper component having an interior and an exterior surface, at least one surface of the additional wrapper component comprising an additional wrapper pattern embossed on at least a portion of a surface of the wrapper component, wherein the additional wrapper pattern is different from the first and second wrapper patterns.

25. The package of absorbent personal care articles of claim 20, wherein a portion of the plurality of absorbent articles comprises a first absorbent article having a first absorbency and a portion of the plurality of absorbent articles comprises a second absorbent article having a second absorbency, wherein the first absorbency is different second absorbency.

26. The package of absorbent personal care articles of claim 20, wherein absorbent articles are selected from the group consisting of sanitary napkins, pantiliners, incontinence pads and incontinence garments.

27. The package of absorbent personal care articles of claim 20, wherein the embossing is visible on the exterior surface of each embossed wrapper component.

28. The package of absorbent personal care articles of claim 20, wherein each wrapper comprises both a printing pattern and an embossing pattern.

29. A method of imparting different embossing patterns to a plurality of articles within a given package, said method comprises providing a plurality of articles for embossing to an embossing roll wherein said articles include a liquid-impermeable garment facing surface and a liquid permeable body facing surface, embossing each of the articles with the embossing roll, wherein the embossing roll comprises a plurality of different embossing patterns arranged in a long repeat pattern so that several articles are embossed before the pattern repeats itself.

* * * * *